United States Patent
Dollinger et al.

[11] Patent Number: 5,891,742
[45] Date of Patent: Apr. 6, 1999

[54] AFFINITY SELECTION OF LIGANDS BY MASS SPECTROSCOPY

[75] Inventors: Gavin D. Dollinger, San Francisco; Verena D. Huebner, Benicia; Surinder Kaur, Lafayette, all of Calif.

[73] Assignee: Chiron Corporation, Emeryville, Calif.

[21] Appl. No.: 375,979

[22] Filed: Jan. 19, 1995

[51] Int. Cl.$^6$ .................................................. G01N 33/537
[52] U.S. Cl. .................... 436/538; 436/528; 436/532; 436/533; 436/534; 436/518
[58] Field of Search .................... 436/518, 528, 436/532, 533, 534, 538, 86, 89

[56] References Cited

U.S. PATENT DOCUMENTS

| | | | |
|---|---|---|---|
| 4,022,876 | 5/1977 | Anbar | 424/1 |
| 4,205,952 | 6/1980 | Cais . | |
| 5,124,267 | 6/1992 | Humpel | 436/518 |
| 5,182,366 | 1/1993 | Huebner et al. . | |

FOREIGN PATENT DOCUMENTS

| | | |
|---|---|---|
| 86/02487 | 4/1986 | WIPO . |
| 91/19735 | 12/1991 | WIPO . |
| 94/06017 | 3/1994 | WIPO . |
| 94/06451 | 3/1994 | WIPO . |
| 94/28145 | 12/1994 | WIPO . |
| 95/04160 | 2/1995 | WIPO . |
| 95/25737 | 9/1995 | WIPO . |

OTHER PUBLICATIONS

Beavis et al. Proc. Natl. Acad. Sci. U.S.A. (1990) 87(17), 6873–7 "Dep. Mass. Spectrom. Gas Phase Ion Chem."

Jung et al. Innovation Perspect. Solid Phase Synth. Collect. Pap. Int. Symp. 2nd (1992) Meeting Date 1991, 227–35. "Modern methods . . . ".

Canty et al. Inorg. Chem. Acta. (1994) 223(1–2) 103–7 "Positive and negative ion electrospray . . . ".

Baczynskyj et al., Rapid. Comm. in Mass. Spectrom. vol. 8, 280–286 1994, "Application of Thermally Assisted Electrospray . . . ".

Lebl et al *Biopolymers* 1995 37(3) 177–98 Abstract only.

*Primary Examiner*—Paula K. Hutzell
*Assistant Examiner*—Heather A. Bakalyar
*Attorney, Agent, or Firm*—Kenneth M. Goldman; Robert P. Blackburn

[57] ABSTRACT

Compounds are quickly selected from a combinatorial library by contacting the library with a target (e.g., receptor), separating non-binding compounds from compound-target complexes, and analyzing the complexes or eluted compound by mass spectroscopy. SAR information is obtained by performing this selection at two or more different ratios of compound to target.

4 Claims, No Drawings

AFFINITY SELECTION OF LIGANDS BY MASS SPECTROSCOPY

DESCRIPTION

Technical Field

This invention relates to the fields of drug discovery and mass spectroscopy. More particularly, the invention relates to the use of mass spectroscopy to identify ligands that bind a selected receptor from a pool of similar ligands.

BACKGROUND OF THE INVENTION

Geysen, EP 198855, disclosed a method for the simultaneous synthesis of a large number of different peptides. Basically, this method involves the synthesis of peptides on a solid polymeric surface, such as polyethylene, which may be molded into the shape of a rod or pin. In a preferred embodiment of the method, these rods or pins are positioned in a holder so that they form a 12 by 8 matrix, with the rods or pins being positioned so that the spacing corresponds to that of the wells of microtiter plates which are widely used for ELISA (enzyme-linked immunosorbent assay) tests.

Huebner et al., U.S. Pat. No. 5,182,366 (incorporated herein by reference) disclosed a method for preparing large mixtures of peptides on solid phase resins in equimolar ratios. This enables one to quickly search for compounds that bind to or react with a ligand by contacting the ligand (e.g., a bound receptor) with a set of peptide mixtures and noting which members of the set bind or react. Typically, the sets are prepared by specifying a known amino acid at one or two positions of an oligopeptide and providing mixtures of amino acids at the other positions. Thus, one peptide mixture might consist of a pool of hexapeptides of the formula Gly-Gly-$X_1$-$X_2$-$X_3$-$X_4$ (SEQ. ID. No.:1), where each X indicates that all amino acids are found at that position. The next peptide mixture would be Gly-Ala-$X_1$-$X_2$-$X_3$-$X_4$ (SEQ. ID. No.:2), followed by Gly-Cys-$X_1$-$X_2$-$X_3$-$X_4$ (SEQ. ID. No.:3), and so forth. The set consisting of all of these mixtures is termed a "library." A library is screened by testing each individual mixture and noting which mixtures produce a positive response. In some formats, the mixtures may be screened simultaneously. The positive mixtures are then resynthesized with additional positions specified. Thus, for example, if the mixture containing Phe-Tyr-$X_1$-$X_2$-$X_3$-X4 (SEQ. ID. No.:4) was positive, the next mixture synthesized might be Phe-Tyr-Gly-$X_2$-$X_3$-$X_4$ (SEQ. ID. No.:5). This process (called "deconvolution") is reiterated until individual peptides are synthesized and tested.

Bartlett et al., WO91/19735, and Zuckermann et al., WO94/06451 disclosed a method for extending combinatorial library synthesis to compounds other than peptides. Bartlett and Zuckermann disclosed modular compounds based on N-substituted polyamides, polycarbamates, and other backbones, which permits one to research non-peptide compounds. These libraries are also analyzed by deconvolution.

DISCLOSURE OF THE INVENTION

We have now invented a method for directly determining the identity of binding ligands by mass spectroscopy, eliminating the need to deconvolute pools of compounds. This permits one analyze combinatorial library results directly, without resynthesizing the mixtures.

Another aspect of the invention is a method for determining the relative affinities of similar active compounds present in a mixture, by selecting compounds at two or more different compound:target ratios and comparing the spectra.

MODES OF CARRYING OUT THE INVENTION

A. Definitions

The term "target" refers to any compound, protein, receptor, or the like, for which a binding or reacting compound is sought. For example, if a library is screened for compounds which bind to the endothelin receptor, the endothelin receptor is the target. The target may be soluble, or immobilized, e.g., on a solid phase or cell surface.

The term "compound" refers to a chemical entity which may be analyzed by mass spectroscopy, and which may have biological activity. Compounds within the scope of this invention preferably have a molecular weight of about 100 to about 1,000 AU, more preferably about 200–900 AU. The term "similar compounds" refers to a set of compounds that are made by substantially the same synthetic method or share certain properties. For example, a mixture of peptides constitutes a set of similar compounds within the scope of this definition. A set of peptoids based on a common backbone is a set of similar compounds, regardless of the difference in polarity, hydrophobicity, pK, or other properties.

The term "mixture of similar compounds" refers to a solution or suspension of similar compounds (as defined above) having at least 10 distinct compounds, more preferably at least 100 different compounds, still more preferably at least 1,000 different compounds.

B. General Method

Affinity selection is conducted using mixtures of compounds, typically resulting from a combinatorial library. The compounds are preferably soluble, rather than bound to a solid phase, and preferably have a molecular weight between about 200 and about 700 Daltons. The compounds may be prepared by any method, preferably as described by Bartlett et al., W091/1973 5, or Zuckermann et al., W094/0645 1, both incorporated herein by reference.

The target may be either bound or soluble, but for kinetic reasons is preferably soluble. The target is typically provided using common techniques of molecular biology. Immobilized targets are provided, for example by expressing a cloned receptor on the surface of a suitable host cell (e.g., a transfected CHO cell or recombinant baculovirus-infected Sf9 cell), or by expressing the receptor in soluble form (e.g., by truncating the receptor so as to exclude a transmembrane anchor domain) and immobilizing it on a suitable surface (for example, by non-specific affinity to nylon or polystyrene assay plates, or by specific binding using antibodies or biotin-avidin coupling systems).

The target and compounds (or library) are brought into contact, either in solution phase or with one component bound to a solid phase, allowed to react or bind, and the non-binding compounds separated from the binding compounds (or compound-target complexes). If the compounds or target are bound to a solid phase, this separation is easily accomplished by washing the solid phase support. If the assay is performed in solution, the separation may be accomplished by means of a sizing column or affinity capture of the target. Sizing columns are generally useful because all compounds in a given library are likely to be of similar size, and are likely to be much smaller than the target or compound-target complex. Affinity capture may be employed, for example, by providing the target with a "tag" or ligand that binds to an antibody or binding partner (e.g., avidin/biotin). It is presently preferred to separate non-bound compounds from compound-target complexes by means of rapid size exclusion chromatography HPLC (SEC-HPLC).

Once separated, the compounds are either eluted from the targets, or are submitted directly for mass spec (MS) analysis. Elution may be accomplished by dilution, pH, competition with a specific ligand, and the like. Some MS ionization methods, such as electrospray, APCI, laser desorption, and electron impact, are sufficient to dissociate the compound from the target, and thus may be used directly, without prior elution. Thus, an SEC-HPLC column may be coupled directly to the input of an ES MS for formation of a rapid throughput instrument. With knowledge of the potential compounds present (i.e., the compounds present in the initial mixture), one can typically identify most or all binding compounds selected from the mixture using an MS detector having a resolution of about 1 A.U.

The exact parameters used (e.g., solvents, temperatures, pH, and the like) will necessarily depend on the compounds and target selected, due to the broad, general nature of the method of the invention and the diversity of possible compounds and targets. However, such parameters may be determined using only routine experimentation, taking as a starting point the physiological conditions under which the compound and target will be expected to interact in vivo. From these initial conditions, one may vary the solvent or carrier to aid in solubilizing hydrophobic targets and/or compounds, and may generally increase temperature, pH, and ionic strength in order to make the assay more stringent. One may begin with about 500 pmol of receptor, and 500 pmol of each compound (about 1 $\mu$M for the mixture as a whole), with or without excess competitive ligand.

Additionally, one may derive structure activity relationships (SAR) by varying the ratio of compound to target. For example, at a ratio of 1:1 compound:target, only the tightest binding compounds will be selected. However, if the ratio is reduced to 0.3:1 compound:target, compounds with lower affinity will also be selected. A comparison of the MS spectra obtained at different ratios thus provides an indication of the relative affinities of the compounds present in the mixture. Compounds which are present in spectra taken at high ratios of compound to target exhibit a high affinity, while compounds present only in spectra taken at low compound:target ratios exhibit an affinity lower than the first group. Taken with knowledge of the compounds selected, this information permits one to rapidly determine which features of the compounds (e.g., presence of hydrophilic or hydrophobic groups, hydrogen bonding, aromaticity) are important for activity. The determination is preferably performed at three or more different ratios of compound to target, for example at ratios of 3:1, 1:1, 0.3:1, 0.01:1, and 0.03:1 compound::target.

C. Examples

The examples presented below are provided as a further guide to the practitioner of ordinary skill in the art, and are not to be construed as limiting the invention in any way.

EXAMPLE 1

(Selection of sUPAR-binding compounds)

Human urokinase plasminogen activator receptor (UPAR) was expressed in a soluble, truncated form as described by Rosenberg et al., WO94/28145, incorporated herein by reference. Peptoid compounds were prepared as described by Bartlett et al., WO91/19735, incorporated herein by reference. Four N-substituted glycine peptoids were prepared, having tyramine in the first (N-terminal) position, 5-aminoindan in the second position, and the following side chains in the third (last) position: diphenyl, phenylphenylether,.indan, and 1,4-benzodioxane. The compounds having diphenyl or phenylphenyl ether in the third position were shown to demonstrate affinity for uPAR (>10 $\mu$M), while the other two compounds demonstrated insignificant activity. The ligand uPA$_{1-48}$ was prepared as described in Rosenberg, supra.

A mixture of 576 N-substituted glycine peptoids was prepared, including the four compounds specified above. The mixture (1 $\mu$M per compound) was contacted with sUPAR (1 $\mu$M) in the presence and absence of uPA$_{1-48}$ (2 $\mu$M), incubated for 30 minutes, and applied to a SEC HPLC column (Pharmacia HSIO/IO). The compound-target complex eluting in the excluded volume of the column was collected and analyzed on an ES MS (PE-Sciex). The results indicated that the same two peptoids (having diphenyl or phenylphenyl ether in the third position) were selected when contacted in the absence of uPA$_{1-48}$: specificity was confirmed by competition in the presence of uPA$_{1-48}$. Identity of the compounds was confirmed by fragmentation in CCID mass spec (collision induced dissociation).

The results demonstrate that even compounds having a relatively low affinity for the target may be quickly and accurately selected without the need for deconvolution.

---

What is claimed:

1. A method for determining the relative affinities of two compounds with respect to a target moiety, said method comprising:

a) providing a mixture of compounds and a target moiety;

b) contacting said target moiety with said mixture of compounds at a first compound:target moiety ratio to form compound-target complexes;

c) separating compounds which do not form complexes with the target moiety from the compound-target complexes;

d) passing said compound-target complexes through a mass spectrometer to obtain a first spectrum;

e) repeating steps a) through d) at a second compound::target moiety ratio different from said first compound::target ratio moiety to obtain a second spectrum; and f) determining the relative affinities of the two compounds that complexed with the target by comparing the first and second spectra, wherein the two compounds have a molecular weight from 100 to 1000 A.U.

2. The method of claim 1, wherein said mixture of compounds comprises a mixture of at least 10 compounds.

3. The method of claim 2, wherein said mixture of compounds comprises a mixture of at least 100 compounds.

4. The method of claim 3, wherein said mixture of compounds comprises a mixture of at least 1,000 compounds.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 3..6
        ( D ) OTHER INFORMATION: /note= ""Xaa"indicates all amino acids."

( x i ) SEQUENCE DESCRIPTION: SEQ ID NO:1:

Gly Gly Xaa Xaa Xaa Xaa
1               5

( 2 ) INFORMATION FOR SEQ ID NO:2:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 3..6
  ( D ) OTHER INFORMATION: /note= ""Xaa"indicates all amino acids."

( x i ) SEQUENCE DESCRIPTION: SEQ ID NO:2:

Gly Ala Xaa Xaa Xaa Xaa
1               5

( 2 ) INFORMATION FOR SEQ ID NO:3:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 3..6
  ( D ) OTHER INFORMATION: /note= ""Xaa"indicates all amino acids."

( x i ) SEQUENCE DESCRIPTION: SEQ ID NO:3:

Gly Cys Xaa Xaa Xaa Xaa
1               5

( 2 ) INFORMATION FOR SEQ ID NO:4:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 3..6
  ( D ) OTHER INFORMATION: /note= ""Xaa"indicates all amino acids."

( x i ) SEQUENCE DESCRIPTION: SEQ ID NO:4:

Phe Tyr Xaa Xaa Xaa Xaa
1               5

( 2 ) INFORMATION FOR SEQ ID NO:5:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear (  i  i  ) MOLECULE TYPE: peptide (  i  x  ) FEATURE:
    ( A ) NAME/KEY: Peptide
    ( B ) LOCATION: 4..6
    ( D ) OTHER INFORMATION: /note= ""Xaa"indicates all amino
        acids."

(  x  i  ) SEQUENCE DESCRIPTION: SEQ ID NO:5:

Phe Tyr Gly Xaa Xaa Xaa
1                5